United States Patent [19]
Ekechukwu

[11] Patent Number: 5,326,451
[45] Date of Patent: Jul. 5, 1994

[54] LIQUID ELECTRODE

[75] Inventor: Amy A. Ekechukwu, Augusta, Ga.

[73] Assignee: The United States of America as represented by the United States Department of Energy, Washington, D.C.

[21] Appl. No.: 2,369

[22] Filed: Jan. 6, 1993

[51] Int. Cl.⁵ .................................... G01N 27/26
[52] U.S. Cl. ........................ 204/416; 204/413; 204/417
[58] Field of Search ............... 204/413, 416, 417, 422, 204/405

[56] References Cited

U.S. PATENT DOCUMENTS

| | | | |
|---|---|---|---|
| 2,706,710 | 4/1955 | Ladisch | 204/195 |
| 2,732,335 | 1/1956 | Glass | 204/1 |
| 3,922,205 | 11/1975 | McLean et al. | 204/413 |
| 4,804,443 | 2/1989 | Newman et al. | 204/413 |
| 4,846,955 | 7/1989 | Osteryoung et al. | 204/413 |

*Primary Examiner*—John Niebling
*Assistant Examiner*—Bruce F. Bell
*Attorney, Agent, or Firm*—Brian R. Tumm; Harold M. Dixon; William R. Moser

[57] ABSTRACT

A dropping electrolyte electrode for use in electrochemical analysis of non-polar sample solutions, such as benzene or cyclohexane. The liquid electrode, preferably an aqueous salt solution immiscible in the sample solution, is introduced into the solution in dropwise fashion from a capillary. The electrolyte is introduced at a known rate, thus, the droplets each have the same volume and surface area. The electrode is used in making standard electrochemical measurements in order to determine properties of non-polar sample solutions.

20 Claims, 1 Drawing Sheet

LIQUID ELECTRODE

The United States Government has rights in this invention pursuant to Contract No. DE-AC09-89SR18035 between the U.S. Department of Energy and Westinghouse Savannah River Company.

BACKGROUND OF THE INVENTION

1. Field of the Invention

The present invention relates to electrodes for electrochemical analysis. More particularly, the present invention relates to electrodes that are drops of conducting liquids for use in making electrochemical measurements of sample solutions.

2. Discussion of Background

In electrochemical analyses, electrodes are used to cause an electrical current to flow through a sample of a solution of interest so that data characteristic of the sample solution can be obtained. Most electrodes used are solid, typically made of metal or other electrically conducting material. However, during repeated use, the surfaces of electrodes tend to erode, reducing the operational accuracy of the device. Further, electrode surfaces tend to accumulate foreign matter caused by the deposit of migrating ions.

Because of these problems, mercury is often used in electrochemical analyses. Typically, mercury, which is liquid at room temperature, is introduced into the sample solution one drop at a time. Thus, a fresh electrode surface is provided by each mercury drop, avoiding the problems of the degradation of the surfaces of solid electrodes.

For example, Ladisch, in U.S. Pat. No. 2,706,710, discloses a polarographic mercury cell used for measuring diffusion currents. His cell has an upper chamber of fritted glass through which mercury drops.

However, the use of mercury in such applications presents health and disposal problems because mercury is highly toxic and therefore requires careful handling and carries with it special disposal requirements. There exists a need for alternate liquid electrodes.

SUMMARY OF THE INVENTION

According to its major aspects and broadly stated, the present invention is an electrode for use in electrochemical analysis of solutions. In particular, the invention is a liquid electrode comprised of a solution of water and a salt such as sodium or potassium chloride for use in electrochemical analysis of non-polar sample solutions, such as benzene or cyclohexane. The liquid electrolyte, immiscible in the sample solution, is introduced into the sample solution in droplets through a glass capillary from a reservoir. The electrolyte is introduced at a known rate, thus providing droplets of known volume and known surface area and, in addition, a fresh electrode surface with each new electrolyte drop formed. The electrodes are used for making standard electrochemical measurements in order to determine electrochemical properties of the sample solution.

A major feature of the present invention is the use of an aqueous salt solution as a working electrode. The advantage of this feature is that the salt solution is non-toxic, unlike mercury. Therefore, the problems of disposing of a hazardous material are eliminated but the benefits of liquid electrodes are preserved.

Other features and advantages of the present invention will be apparent to those skilled in the art from a careful reading of the Detailed Description of a Preferred Embodiment presented below and accompanied by the drawings.

DETAILED DESCRIPTION OF PREFERRED EMBODIMENTS

Figure 1:
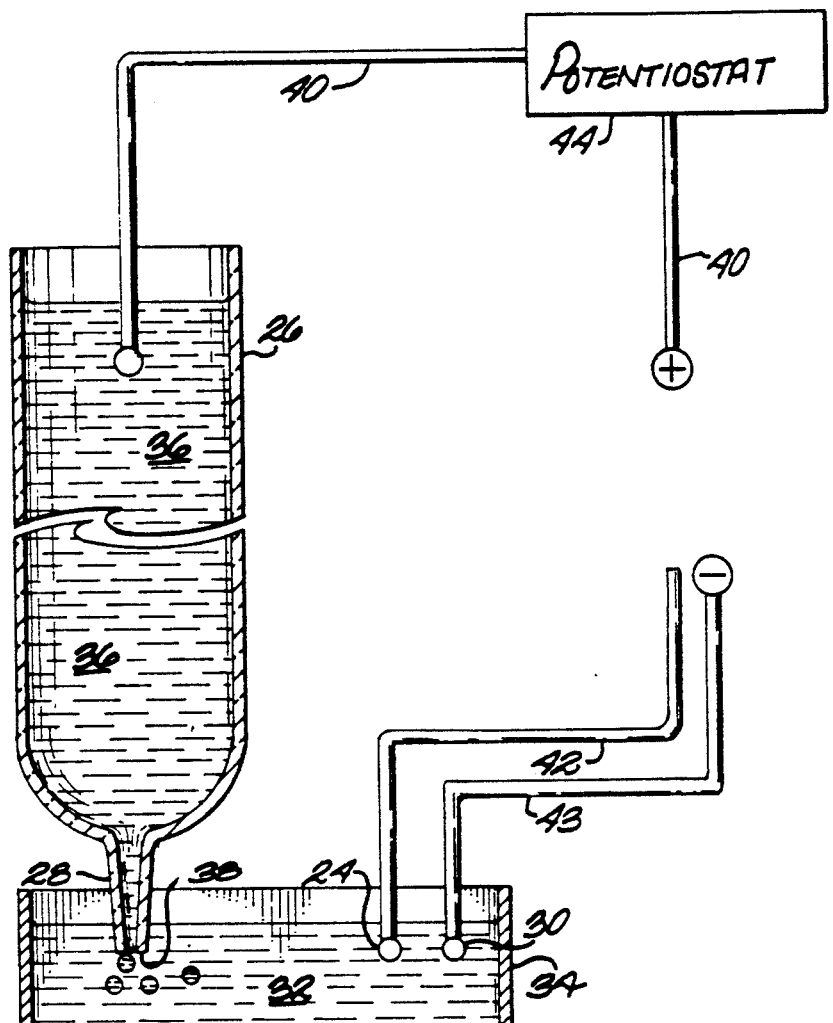
FIG. 1 is a side, cross-sectional view of a dropping electrolyte electrode according to a preferred embodiment of the present invention.

In the following description similar components are referred to by the same reference numeral in order to simplify the understanding of the sequential aspect of the drawings.

In typical electrochemical analysis, a sample of a solution to be analyzed is placed in a container, or electrocell. The electrocell has a pair of electrodes, usually a working electrode and an auxiliary electrode, that are placed in the sample solution. (A reference electrode may also be used if more extensive measurement data is sought.) The working and auxiliary electrodes are spaced apart from one other and an electric potential is applied across them whereby a current flows through the solution from one electrode to the other.

As the potential difference across the electrodes is varied over a preselected range, a correspondingly varying current flows through the sample solution. The current results from oxidation and reduction reactions of the constituents of the sample solution. The voltage-to-current relationship of the sample solution, which are characteristic of the particular types of substances present in the solution and their concentrations, are measured by standard measuring devices and interpreted to determine properties of the sample solution, such as, in particular, the concentrations and types of ions present.

Referring now to FIG. 1, the apparatus for electrochemical analysis 20 in its preferred embodiment has an auxiliary electrode 24 and a working electrode comprising a reservoir 26 and a capillary 28. Also, a reference electrode 30 may be included for additional measurement capability. A sample solution 32 to be analyzed is contained within an electrocell 34, or other container.

Reservoir 26 is preferably a hollow body made of an insulating material, such as glass, and carrying an electrolyte 36 within its interior. Capillary 28 has a proximal end 30 and a distal end 38 and is preferably an extension of reservoir 26 with proximal end 30 in fluid communication with reservoir 26 and distal end 38 extending into sample solution 32 when reservoir 26 is operably positioned so that electrolyte 36 can flow from the interior of reservoir 26 through capillary 28 from proximal to distal ends. Auxiliary electrode 24 is also positioned in sample solution 32, preferably spaced apart from capillary 28.

A positive terminal lead 40 extends out of reservoir 26 and preferably connects to an electric potential source (not shown). Similarly, a negative terminal lead line 43 extends from reference electrode 30 and connects to the electrical potential source. Auxiliary electrode 24 has a separate lead line 42 extending to the electrical potential source.

Any standard means for controlling current flow, such as a potentiostat 44, can be connected in series with positive terminal lead 40 to vary the amount of current flowing between the working electrode and auxiliary electrode 24, thus varying the amount of current flowing through sample solution 32. A potentiometer (not shown) or other instrumentation is then used to determine certain electrochemical properties of sample solution 32.

Electrolyte 36 contained in reservoir 26 is preferably a polar electrolytic solution. Also, electrolyte 36 should be a solution of the kind that is immiscible in sample solution 32. For example, if sample solution 32 is non-polar, such as benzene or cyclohexane, then electrolyte 36 should be a polar electrolyte, preferably an aqueous salt solution, such as sodium chloride or potassium chloride, which are both electrically conducting and non-toxic.

Figure 2:
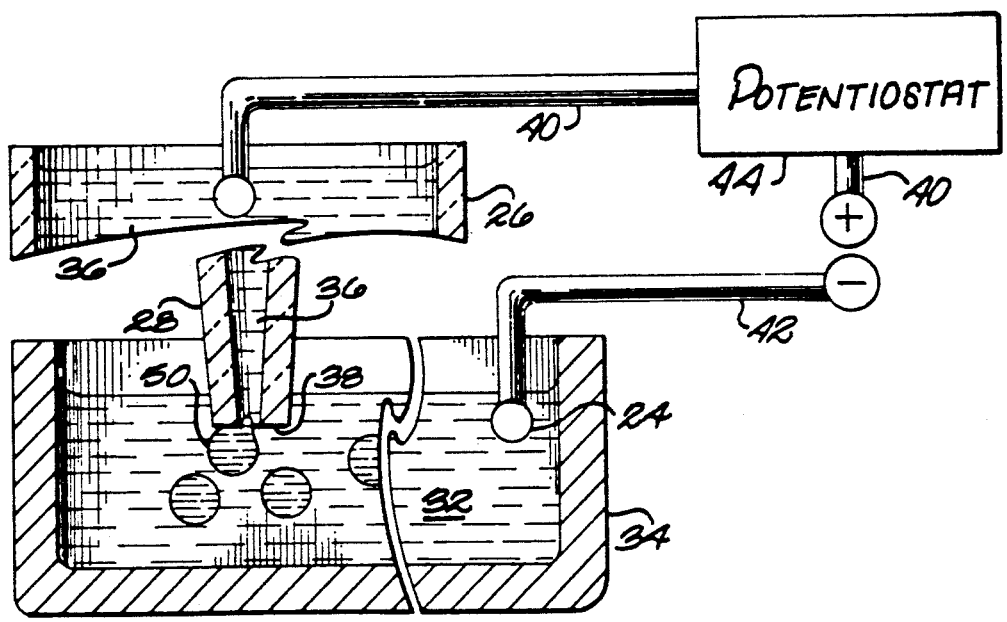
FIG. 2 is a partial cross-section of the electrode of FIG. 1 at the end of the capillary showing the electrolyte being released into the sample solution.

Referring to FIG. 2, capillary 28 is preferably constructed so that, during operation, capillary 28 releases droplets of electrolyte 36 into sample solution 32 at a constant rate. Since electrolyte 36 is preferably immiscible in sample solution 32, a previously released droplet 50 of electrolyte 36 from capillary 28 maintains its shape and integrity in sample solution 32, thus, the concentration of ions in sample solution—and its conductivity—are not affected by the electrolytic droplets. Each droplet has a known volume and a known surface area that can be readily calculated from the amount of electrolyte used per droplet.

Capillary 28 is preferably made of an electrically insulating material, such as glass, so that current flow from an applied electric potential travels from a droplet 50 currently being released from capillary 28 to sample solution 32. Thus, during current flow, the newly formed surface of droplet 50 is in direct physical and electrical contact with sample solution 32. Each droplet 50 brings with it a new surface and the droplets are continually being formed.

In use, sample solution 32 is placed in cell 34 for analysis. Cell 34 is positioned with respect to reservoir 26 so that capillary 28 extends into sample solution 32. Also, auxiliary electrode 24, via negative terminal lead 42, is placed in sample solution 32.

Then, an electric potential is applied across electrolyte 36 and auxiliary electrode 24, using terminal leads 40, 42. The amount of current flowing from electrolyte 36, through sample solution 32, to auxiliary electrode 24 is measured by current measuring device 44. As previously discussed, the amount of current flowing through sample solution 32 for a given electrical potential is a function of the concentration of certain ions in sample solution 32.

In a typical analysis procedure, the magnitude of the electric potential applied between electrolyte 36 and auxiliary electrode 24 is varied in discrete steps over a predetermined range of electric potentials. The change in the current flowing through sample solution 32 and the actual potential at which this change occurs is measured and recorded. The current/voltage relationships are compared to reference data to determine the electrochemical properties of sample solution 32.

It will be apparent to those skilled in the art that many changes and substitutions can be made to the preferred embodiment herein described without departing from the spirit and scope of the present invention as defined by the appended claims.

What is claimed is:

1. Apparatus for electrochemical analysis of ions in a solution, said apparatus comprising:

a cell, said solution contained by said cell;
 an auxiliary electrode in said solution;
 a reservoir which contains a polar electrolyte, feeds said polar electrtrolyte into said solution at a spaced apart distance from said auxiliary electrode, said electrolyte being immiscible in said solution; and
 means for applying an electrical potential between said electrolyte and said auxiliary electrode.

2. The apparatus as recited in claim 1, wherein said electrolyte is an aqueous salt solution.

3. The apparatus as recited in claim 1, wherein said electrolyte is selected from the group consisting of sodium chloride and potassium chloride.

4. The apparatus as recited in claim 1, further comprising means for releasing said electrolyte into said solution in a dropwise fashion, said releasing means releasing said electrolyte so that said electrolyte droplets formed have uniform volume.

5. The apparatus as recited in claim 1, further comprising means for releasing said electrolyte into said solution, wherein said releasing means further comprises:

a reservoir made of electrically insulating material and having an interior; and
 a capillary formed at one end of said reservoir and having a proximal end and a distal end, said proximal end in fluid communication with said interior of said reservoir so that said electrolyte in said reservoir can flow from said reservoir through said capillary from said proximal end to said distal end, said distal end submerged in said solution.

6. The apparatus as recited in claim 1, further comprising means for varying said applied potential stepwise over a set range.

7. The apparatus as recited in claim 1, further comprising means for releasing said electrolyte into said solution, wherein said releasing means further comprises:

said reservoir made of electrically insulating material and having an interior; and
 a capillary made of electrically insulating material, said capillary formed at one end of said reservoir and having a proximal end and a distal end, said proximal end in fluid communication with said interior of said reservoir so that said electrolyte in said reservoir can flow from said reservoir through said capillary from said proximal end to said distal end, said distal end submerged in said solution.

8. Apparatus for electrochemical analysis of ions in non-polar sample solutions, said apparatus comprising:

a cell, said sample solution contained by said cell;
 an auxiliary electrode positioned in said sample solution;
 a polar electrolyte;
 a working electrode containing said electrolyte and spaced apart from said auxiliary electrode, said working electrode having means formed therein for releasing said electrolyte into said sample solution in a dropwise fashion; and
 means for applying an electrical potential across said auxiliary and working electrodes so that an electrical current flows through said sample solution.

9. The apparatus as recited in claim 8, wherein said electrolyte is an aqueous salt solution.

10. The apparatus as recited in claim 8, wherein said electrolyte is immiscible in said sample solution.

11. The apparatus as recited in claim 8, wherein said electrolyte is a solution of water and a salt selected from the group consisting of sodium chloride and potassium chloride.

12. The apparatus as recited in claim 8, wherein said working electrode further comprises means for releasing said electrolyte so that said electrolyte droplets formed have uniform volume, said electrolyte droplets forming a new surface of said electrolyte with each droplet.

13. The apparatus as recited in claim 8, wherein said working electrode further comprises:
   a reservoir made of electrically insulating material which contains said electrolyte, said reservoir having an interior; and
   a capillary having a proximal end and a distal end, said proximal end in fluid communication with said interior of said reservoir so that said electrolyte can flow from said interior through said capillary from said proximal end to said distal end, said distal end submerged in said solution.

14. The apparatus as recited in claim 8, further comprising means for varying said applied potential stepwise over a set range.

15. The apparatus as recited in claim 8, wherein said second electrode further comprises:
   a reservoir which contains said electrolyte, said reservoir made of electrically insulating material and having an interior; and
   a capillary made of electrically insulating material, said capillary formed at one end of said reservoir and having a proximal end and a distal end, said proximal end in fluid communication with said interior of said reservoir so that said electrolyte will flow from said interior through said capillary from said proximal end to said distal end, said distal end submerged in said solution.

16. A method for electrochemical analysis of ions in a non-polar sample solution, said method comprising the steps of:
   positioning an auxiliary electrode in a cell containing said sample solution;
   positioning a working electrode in spaced relation to said auxiliary electrode and in electrical communication with said sample solution, said working electrode having means for releasing droplets of a polar electrolyte into said sample solution;
   releasing said droplets into said sample solution; and
   applying an electrical potential across said electrolyte and said auxiliary electrode.

17. The method as recited in claim 16, wherein said electrolyte is an aqueous salt solution immiscible in said sample solution.

18. The method as recited in claim 16, wherein said electrolyte is immiscible in said sample solution.

19. The method as recited in claim 16, wherein said electrolyte is a solution of water and a salt selected from the group consisting of sodium chloride and potassium chloride.

20. The method as recited in claim 16, further comprising the step of varying said applied potential stepwise over a set range.

* * * * *